United States Patent
Yao (10) Patent No.: US 8,500,639 B2
(45) Date of Patent: Aug. 6, 2013

(54) SYSTEMS AND METHODS FOR SHEAR WAVE FIELD FORMATION

(75) Inventor: Lin Xin Yao, Renton, WA (US)

(73) Assignee: MR Holdings (HK) Limited, Hong Kong (CN)

( * ) Notice: Subject to any disclaimer, the term of this patent is extended or adjusted under 35 U.S.C. 154(b) by 403 days.

(21) Appl. No.: 12/878,346

(22) Filed: Sep. 9, 2010

(65) Prior Publication Data

US 2011/0066030 A1 Mar. 17, 2011

Related U.S. Application Data (60) Provisional application No. 61/241,817, filed on Sep. 11, 2009.

(51) Int. Cl.
*A61B 8/00* (2006.01)

(52) U.S. Cl.
USPC .......................................... 600/438; 600/437

(58) Field of Classification Search
USPC ................................. 600/437–438
See application file for complete search history.

(56) References Cited

U.S. PATENT DOCUMENTS

2010/0069751 A1* 3/2010 Hazard et al. ............... 600/438

OTHER PUBLICATIONS

Bercoff, Jeremy, "ShearWave Elastography", 2008, Supersonic Imagine Whitepaper, pp. 1-11.*
Bercoff et al, "Supersonic Shear Imaging: A New Technique for Soft Tissue Elasticity Mapping", IEEE 2004, pp. 396-409.*
Lazebnik et al., "Tissue Strain Analytics Virtual Touch Tissue Imaging and Quantification", Siemens Whitepaper, Oct. 2008, pp. 1-5.*

* cited by examiner

*Primary Examiner* — James Kish
*Assistant Examiner* — Christopher Cook
(74) *Attorney, Agent, or Firm* — Kory D. Christensen; Stoel Rives LLP (57) ABSTRACT

An ultrasound imaging system provides dynamic control of a shear wave front used to image viscoelasticity in a biological tissue. The system receives an indication of a region of interest and selects a shear wave front shape. The system also selects, based on the selected shear wave front shape, focus locations for a plurality of push pulses and a sequence for moving a shear wave source among the focus locations. The system transmits a series of push pulses according to the selected sequence, and determines a speed of the shear wave front as it passes through the region of interest. Changes in the speed of the shear wave front are related to changes in stiffness within the tissue.

26 Claims, 7 Drawing Sheets

SYSTEMS AND METHODS FOR SHEAR WAVE FIELD FORMATION

CROSS-REFERENCE TO RELATED APPLICATION

This application claims the benefit under 35 U.S.C. §119 (e) of U.S. Provisional Patent Application No. 61/241,817, filed Sep. 11, 2009, which is hereby incorporated by reference herein in its entirety.

TECHNICAL FIELD

This disclosure relates to medical imaging. In particular, this disclosure relates to imaging tissue based on shear acoustic waves.

SUMMARY

An ultrasound imaging system according to one embodiment provides dynamic control of a shear wave front used to image viscoelasticity in a biological tissue. The system receives an indication of a region of interest and selects a shear wave front shape. The system also selects, based on the selected shear wave front shape, focus locations for a plurality of push pulses and a sequence for moving a shear wave source among the focus locations. The system transmits a series of push pulses according to the selected sequence, and determines a speed of the shear wave front as it passes through the region of interest. Changes in the speed of the shear wave front are related to changes in stiffness within the tissue.

Additional aspects and advantages will be apparent from the following detailed description of preferred embodiments, which proceeds with reference to the accompanying drawings.

DETAILED DESCRIPTION

Determination of relative tissue stiffness is used to diagnose diseases and monitor therapies. Manual palpation may be used to detect stiff lesions or structures that may not be evident using conventional imaging technology, such as conventional B-mode sonography. Manual palpation may be limited, however, to accessible tissues. Thus, the field of elastography has developed techniques for generating images related to tissue stiffness. These techniques may include, for example, strain elastography, transient elastography, vibroacoustography, and ultrasonic shear wave elasticity imaging.

In ultrasonic shear wave elasticity imaging, a transmitted acoustic "push pulse" focused at a remote location within biological tissue applies an acoustic force inside the tissue and produces a shear wave in the transverse direction with respect to the propagation direction of the push pulse. The focus point of the push pulse inside the tissue may be referred to herein as a "shear wave source." The shear wave induces measurable displacement as a function of time that may be linked to the local viscoelasticity of the tissue.

To increase the strength of the shear wave, which results in increased displacement of the tissue, "supersonic" shear wave elasticity imaging uses multiple push pulses. The transmitted push pulses are tightly focused at sequential locations within the tissue. Thus, the shear wave source sequentially moves from one focus location to the next. Generally, the shear wave source moves from shallow tissue locations to deeper tissue locations at a speed that is greater than the shear wave propagating speed (about 2 m/s). In other words, the shear wave source moves at a supersonic speed with respect to the propagation speed of the shear wave. A wave front of the combined shear waves from the multiple push pulses forms a "supersonic cone." Detection of the wave front with respect to time determines the local shear wave speeds and the characteristics of the local tissue.

The systems and methods disclosed herein form controllable shear wave fronts that may be directed to selected locations and that may include selectable wave front shapes and/or strengths. In one embodiment, a method for imaging viscoelasticity in a tissue uses a dynamically controlled shear wave front produced by an ultrasound imaging system. The method includes receiving an indication of a region of interest within the tissue and selecting a shape of a shear wave front to pass through the region of interest. In certain embodiments, the wave front shape is selected so as to increase the shear wave strength at the region of interest. The method also includes selecting, based on the selected shear wave front shape, a plurality of focus locations within the tissue and a sequence in which to move a shear wave source between the selected focus locations. The method also includes transmitting, into the tissue, a series of focused ultrasonic push pulses from a transducer array based on the selected sequence. Each push pulse remotely generates a respective shear wave at one of the selected focus locations. The respectively generated shear waves interact with one another as the shear wave source moves between the focus locations to produce an overall shear wave having the selected shear wave front shape. The method also includes imaging, using the transducer array, the shear wave front as it travels through the region of interest.

In one embodiment, the method further includes selecting a focal point within the tissue, wherein the selected shear wave front shape corresponds to a circular shape centered at the focal point. In such an embodiment, selecting the sequence may include alternating the shear wave source between deep and shallow focus locations within the tissue while progressively moving the shear wave source toward a central focus location.

The plurality of focus locations may be selected to be along a straight line substantially parallel to a propagation direction of the push pulses. In such an embodiment, the method may include transmitting a first push pulse focused at a first focus location and delaying transmission of a second push pulse after the transmission of the first push pulse. The second push pulse is focused at a second focus location. The delay is for a time period substantially equal to a difference between a first time of flight and a second time of flight. The first time of flight corresponds to a first shear wave traveling between the first focus location and the focal point. The second time of flight corresponds to a second shear wave traveling between the second focus location and the focal point. After the delay, the method includes transmitting the second push pulse.

In another embodiment, selecting the plurality of focus locations includes defining the plurality of focus locations along a curved path within the tissue. In such an embodiment, the curved path may be based on transmitting the series of push pulses at a constant rate so as to generate a circular shear wave front shape. Selecting the plurality of focus locations may include defining an arc of the circular shear wave front shape, placing a first focus location on the arc at a first depth within the tissue corresponding to a depth of the focal point, and placing a second focus location at a second depth within the tissue and at a distance from the arc corresponding to a propagation delay based on the constant rate used to transmit the series of push pulses.

In another embodiment, selecting the plurality of focus locations includes defining the plurality of focus locations along a straight line offset at an angle with respect to a propagation direction of the push pulses. In such an embodiment, the series of push pulses may be transmitted at respective times such that the shear wave front shape is planar.

In certain embodiments, receiving an indication of a region of interest includes generating, using the ultrasound imaging system, a B-mode ultrasound image of the tissue, and allowing a user to place a marker on the B-mode ultrasound image to define the region of interest.

In certain embodiments, a beamformer of the ultrasound imaging system may be used to weight the transmitted push pulses. The beamformer may also be used to focus the transmitted push pulses at individual points, along lines, and/or within a group of points or regions. In addition, or in other embodiments, the beamformer may be used with limited diffraction technology for imaging.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

Figure 1:
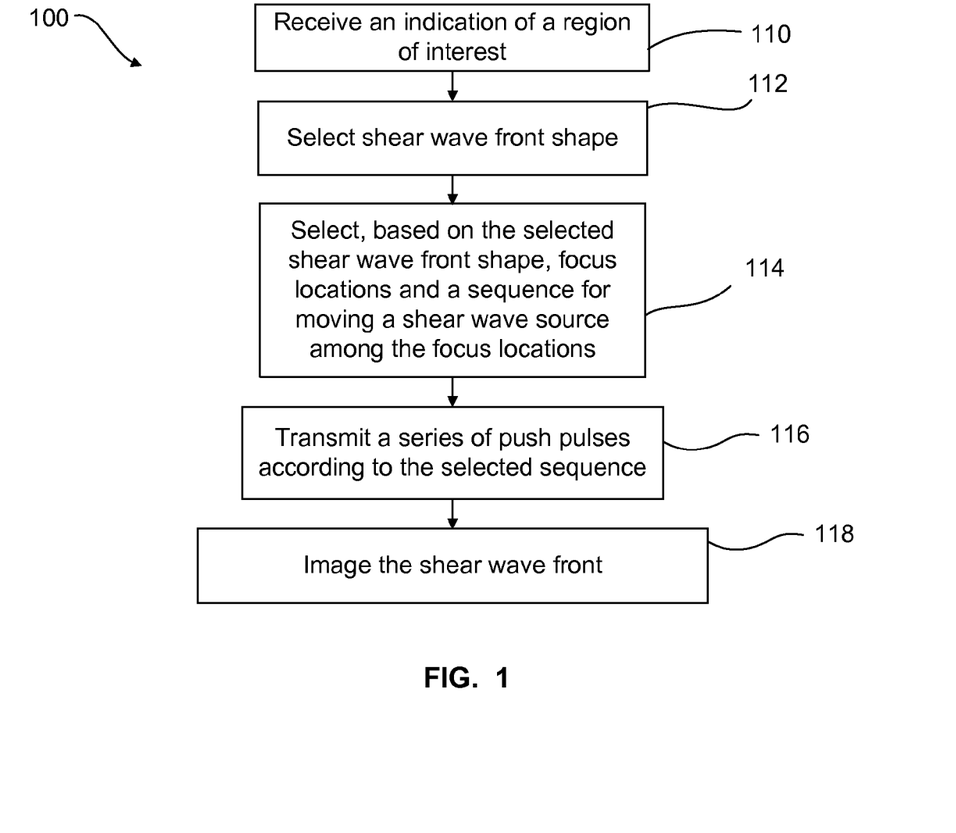
FIG. 1 is a flowchart of a method for imaging viscoelasticity in biological tissue using a dynamically controlled shear wave front according to one embodiment.

FIG. 1 is a flowchart of a method 100 for imaging viscoelasticity in biological tissue using a dynamically controlled shear wave front according to one embodiment. The method 100 includes receiving 110 an indication of a region of interest within the tissue. The region of interest may be selected, for example, by a user of an ultrasound imaging system. The method 100 also includes selecting 112 a shear wave front shape. In certain embodiments, the shear wave front shape is selected by the user of the ultrasound imaging system. In other embodiments, the ultrasound imaging system selects the shear wave front shape automatically, without user intervention, based on the indication of the region of interest. For example, the ultrasound imaging system may select from a plurality of predetermined shear wave front shapes based on the location, size, tissue characteristics, and/or other properties of the indicated region of interest.

The method 100 also includes selecting 114, based on the selected shape, focus locations and a sequence for moving a shear wave source among the focus locations. As discussed in detail below, the selected shear wave front shape is controlled by the selection of the focus locations and the sequence. In certain embodiments, the ultrasound imaging system automatically, without further user intervention, determines the focus locations and sequence to be used in forming the desired wavefront shape, strength, direction of propagation, and/or other shear wave properties. In addition, or in other embodiments, the user may select at least some of the focus locations and/or portions of the sequence. In addition to the order in which the shear wave source moves among the selected focus locations, the sequence may define parameters such as delays between transmitted push pulses, weighting (e.g., energy) of individual push pulses, and/or focus area size of each push pulse.

The method 100 also includes transmitting 116 a series of push pulses according to the selected sequence. As mentioned above, these pulses may also be weighted by the beamformer. Each transmitted push pulse generates a respective shear wave at one of the selected focus locations. The plurality of generated shear waves interact with one another within the tissue to produce a shear wave front (e.g., through positive interference) having the selected shape. The method further includes imaging 118 the shear wave front as it travels through the region of interest. In certain embodiments, the ultrasound imaging system applies tracking beams adjacent to the push pulse path to detect the passing shear wave front. The time between the generation of the shear wave front and detection of a peak associated with the shear wave front is used to compute the shear wave velocity. The value of the velocity of the shear wave front is related to the stiffness of the tissue within the region of interest. Accordingly, the stiffness may be quantized and superimposed, in certain embodiments, on a B-mode ultrasound image of the region of interest.

Figure 2:
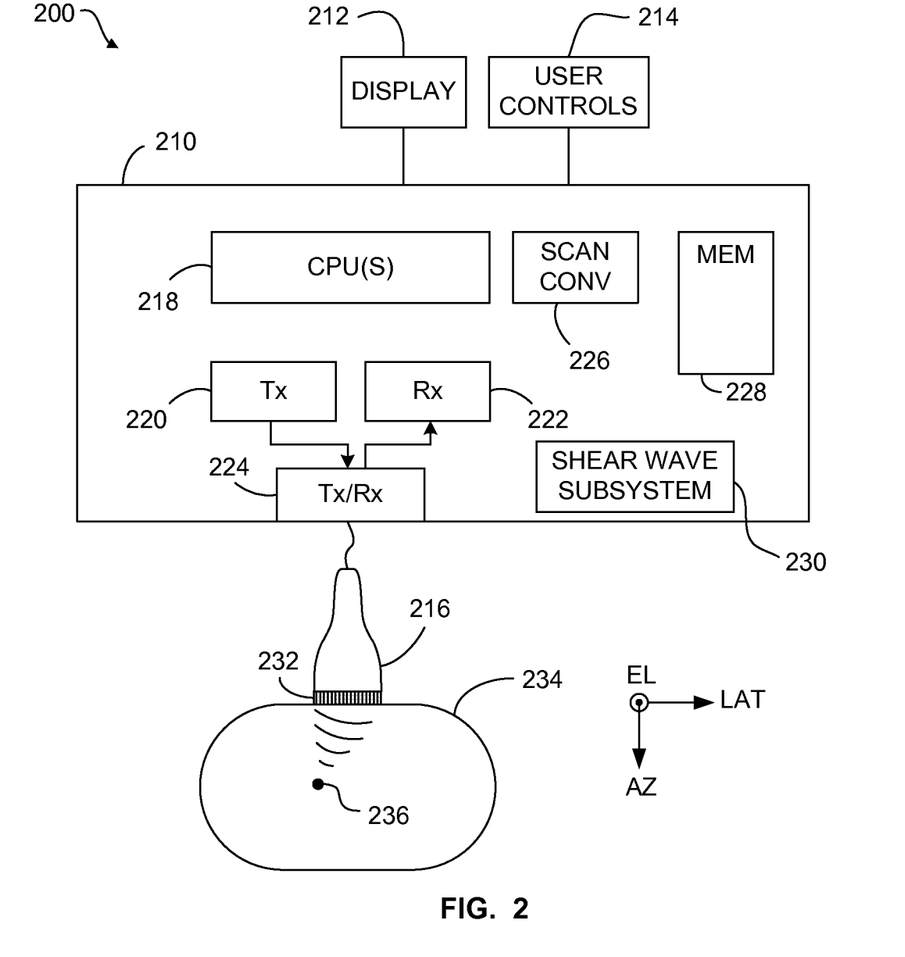
FIG. 2 is a block diagram of an ultrasound imaging system configured to image viscoelasticity in biological tissue according to one embodiment.

FIG. 2 is a block diagram of an ultrasound imaging system 200 configured to image viscoelasticity in biological tissue according to one embodiment. The system 200 includes a main processing system 210, a display device 212 for displaying ultrasound images, user controls 214, and an ultrasonic probe or transducer 216. The user controls 214 allow a user to enter various scan parameters and selections associated with a desired region of interest and/or shear wave front, as discussed herein. The user controls 216 may include conventional hardware, system software, and devices such as a keyboard, knobs, a mouse, and/or buttons.

The processing system 210 may include an electrically connected and cooperating group of processors 218 such as microprocessors and digital signal processors with necessary system software such as, for example, an operating system. The processing system 210 also includes a transmission control circuit 220, a reception controller 222, a switching circuit 224, a scan converter 226, a memory device 228, and a shear wave subsystem 230.

The processing system 210 sets, adjusts, and monitors the operating parameters of the transmission control circuit 220. The transmission control circuit 220 generates and applies electrical control and driving signals to the transducer 216, which includes an array of electro-acoustic (usually piezoelectric, such as PZT) elements 232. The array of elements 232 generate ultrasonic waves when electrical signals of the proper frequency are applied to them. In certain embodiments, as discussed herein, the array of elements 232 generate a series of push pulses at selected focus locations.

To create the ultrasonic signals that are transmitted into the body (e.g., at an "interrogation region" 234), all or some subset of the elements 232 are electrically excited at a given frequency and are individually phased and time-shifted relative to each element's position in the array in such a way that the in-phase portions of the signals form a coherent transmit (Tx) beam. The time delays are chosen such that the echo signals arriving from a desired angular direction add coherently, whereas those signals arriving from other directions do not add coherently and so tend to cancel each other out. The amplitudes of the excitation signals applied to the array elements 232 may be varied (apodized) to control the resulting beam width and to suppress side lobes. The aperture of the array may also be varied, that is, the "width" of the activated elements (not all elements are usually activated at once) may be changed, just as the aperture of a camera may be varied to affect focal depth and provide uniform lateral resolution.

Various methods for activating the elements 232 according to a particular signal profile to image a given area are generally referred to as transmit beamforming. By changing the amplitude and phasing of the transmitted signals, the Tx beam can be not only focused at a particular depth, but also steered off-axis, that is, not perpendicular to the center element among those activated. In FIG. 2, for example, the Tx beam has been steered at an angle to the face of the array elements 232. Out-of-phase portions of the individual transmit signals tend to cancel each other. The Tx beam converges at a focal depth, beyond which it once again diverges. The Tx beam is steered in the azimuth/lateral direction LAT and the elevation direction EL, and is focused in the depth/axial direction AX so as to concentrate the ultrasonic energy of the beam onto desired points, such as a focus point 236, within the interrogation region 234.

After transmission, the transducer 216 may be switched by the switching circuit 224 from the transmit mode to a receive mode, such that the ultrasound reflected back onto the array face from any structures within the imaged area will cause the elements 232 to create corresponding electrical signals. The ultrasound sensed by any particular element 232, however, will be a combination of all the ultrasound energy reflected back from anywhere in the imaged region, regardless of which elements 232 the energy originated from. In the general case, each element 232 will receive some ultrasound energy created by all elements 232 that were energized to form the Tx beam. In the receive (Rx) mode, each element 232 will therefore generate a time-varying signal that in practice will differ from that of all other elements' received signals. Again, however, the in-phase portion of the reflected energy will dominate. A receive beamformer (not shown) determines and sums the coherent signals from targets received by all the active Rx array elements 232.

The piezoelectric array elements 232 convert the small mechanical vibrations caused by the echo signal into corresponding radio-frequency (RF) electrical signals. Amplification and other conventional signal conditioning are then applied to the return signals by a reception controller 222. This processing includes various procedures as needed to identify the echo signals that correspond to each scanned element in the interrogation region 234 and form the Rx beam for each channel. The reception controller 222, all or part of which is normally integrated into the processing system 210 itself, also converts the ultrasonic, radio-frequency (RF) return signals (typically on the order of a few megahertz to tens of megahertz) into lower frequency ranges for processing. Note that the transmission and reception controllers (or, for that matter, transmit and receive beamformers) do not have to be implemented as separate components but may be combined in whole or in part with respect to both their hardware and software.

In conventional B-mode scanning, each point within the interrogation region 234 is then represented as an intensity (brightness) value. The interrogation region 234 can therefore be represented as a discretized pattern (matrix) of brightness or signal intensity values, which are stored as frame data in a memory 228. Other scan modes, such as for Doppler imaging, create and store corresponding values.

The shear wave subsystem 230 allows the ultrasound imaging system 200 to operate in a shear wave mode. In certain embodiments, the shear wave subsystem 230 determines the focus locations and sequence for moving a shear wave source among the focus locations. In addition, or in other embodiments, the shear wave subsystem 230 performs the other functions described herein with respect to dynamically controlling the shear wave front. An artisan will recognize from the disclosure herein that the shear wave subsystem 230 may be combined with other components of the ultrasound imaging system 200. For example, at least some of the functions described for the shear wave subsystem 230 may be performed by the processors 218.

For tissue quantification according to one embodiment, the shear wave subsystem 230 may allow the user of the ultrasound imaging system 200 to identify an anatomic location for measurement using a region of interest marker placed on an ultrasound image. An acoustic push pulse is applied just lateral to this location, inducing a shear wave that travels through the region of interest. Tracking beams, sensitive to greater than $1/100$ the wavelength of sound, are applied to the pulse path. The tracking beams are continuously transmitted until the passing shear wave front is detected. The time between generation of the shear wave and detection of the peak is utilized to compute the shear wave velocity. Multiple measurements are made for a given spatial location before a value is reported in order to ensure measurement quality.

Figure 3:
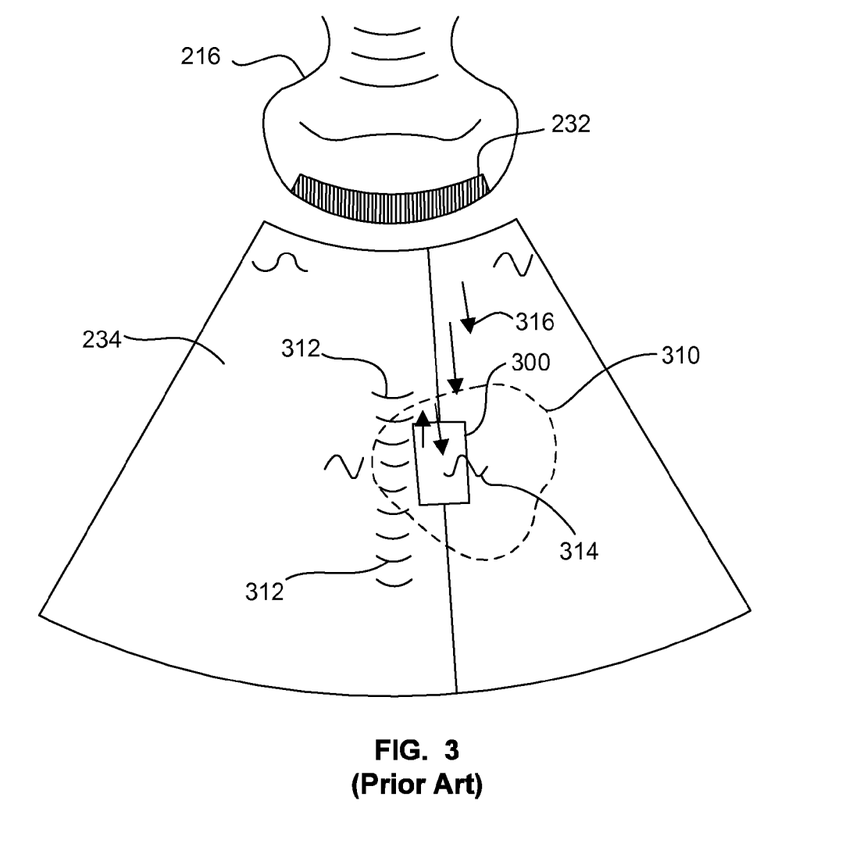
FIG. 3 is a schematic diagram illustrating a transducer operating on a soft tissue interrogation region according to one embodiment.

FIG. 3 is a schematic diagram illustrating a transducer 216 operating on a soft tissue interrogation region 234 according to one embodiment. As conceptually shown in FIG. 3, a user may indicate a region of interest 300 where a suspected or confirmed stiff legion 310 exists within the soft tissue. The array of elements 232 in the transducer 216 transmits acoustic push pulses 312 laterally adjacent to the indicated region of interest 300. The push pulses 312 generate shear waves 314 that pass through the region of interest 300. When detection pulses 316 interact with a passing shear wave 314, the interaction reveals the shear wave's location at a specific time, which allows calculation of the shear wave's speed. The numerical value of the shear wave's speed is related to the stiffness of the tissue within the region of interest 300. In certain embodiments, the shape of the shear wave front is dynamically controlled to improve the strength of the shear wave 314 in the region of interest, which improves the ability to determine the speed of the shear wave 314.

Figure 4:
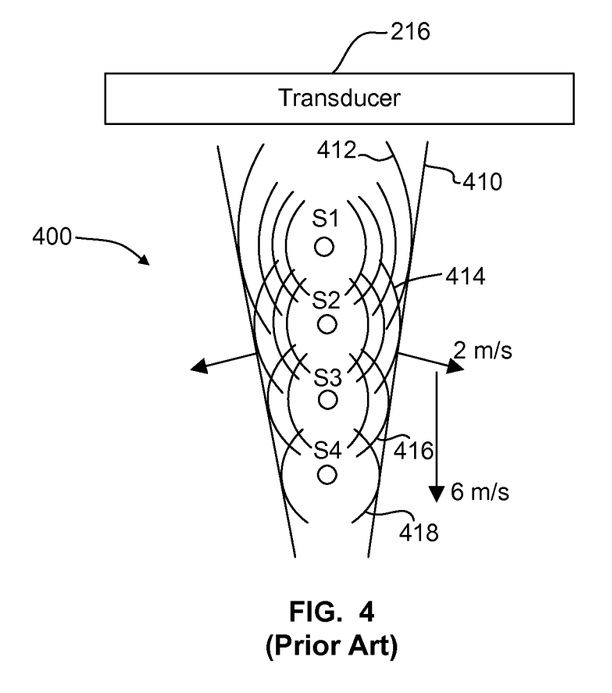
FIG. 4 is a schematic diagram illustrating four shear wave sources generated within biological tissue according to one embodiment.

FIG. 4 is a schematic diagram illustrating four shear wave sources S1, S2, S3, S4 generated within biological tissue according to one embodiment. As discussed above, each shear wave source S1, S2, S3, S4 is generated by a respective push pulse (not shown) transmitted from a remote transducer 216. The transmission, in turn, of each push pulse is tightly focused at a selected focus location corresponding to the respective shear wave sources S1, S2, S3, S4. As shown in the example of FIG. 4, the push pulse focus locations are set from shallower to deeper at a speed greater than the shear wave propagating speed (about 2 m/s). For example, the sequence of push pulses may move at a speed of about 6 m/s from S1 to S2, then from S2 to S3, and then from S3 to S4. Thus, the shear wave sources S1, S2, S3, S4 move faster than the shear wave propagating speed, which qualifies as "supersonic." A "Mach number" is the ratio of the moving speed of the shear wave sources S1, S2, S3, S4 to the shear wave propagating speed. A wave front 410 of the combined shear waves 412, 414, 416, 418 from the multiple push pulse focal points forms a "supersonic cone." Detection of the wave front 410 with time determines the local shear wave speeds and the characteristics of the local tissue.

As disclosed herein, the shape of the wave front 410 may be selected by a user or an ultrasonic imaging system. In the example 400 shown in FIG. 4, the wavefront 410 of the overall shear wave is planar. The tilt of the planar wavefront 410 may be changed by reversing the order of the sequence and/or by changing the speed at which the shear wave source moves from one focus location to the next. According to other embodiments, however, the shape of the wave front 410 may be selectively changed by rearranging the sequence of the push pulse focal points and/or by selecting a non-linear arrangement of focus locations.

Figure 5:
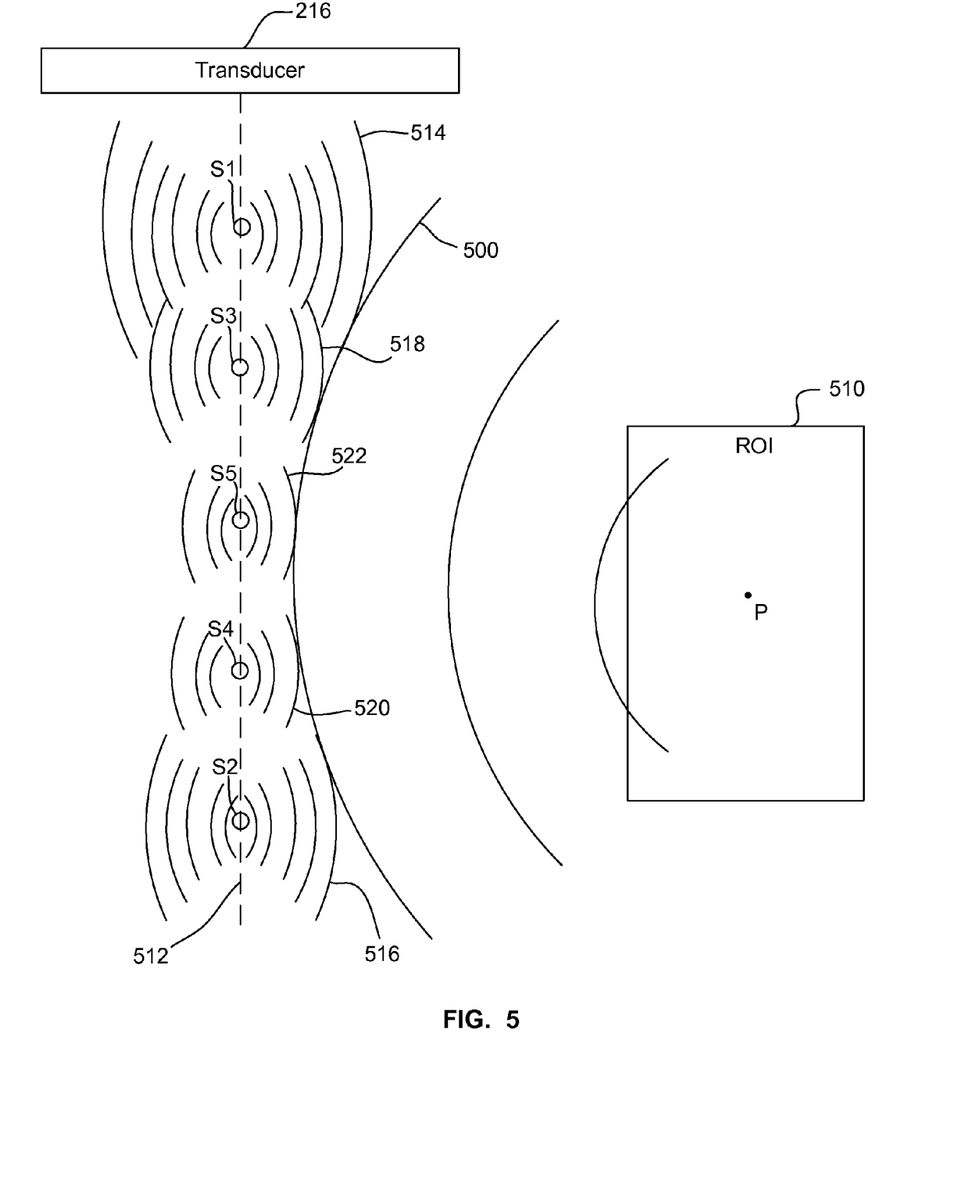
FIG. 5 is a schematic diagram illustrating a sequence of shear wave sources generated within biological tissue according to another embodiment.

For example, FIG. 5 is a schematic diagram illustrating a sequence of shear wave sources S1, S2, S3, S4, S5 generated within biological tissue according to another embodiment. In the embodiment shown in FIG. 5, the selected wavefront shape is circular to increase or maximize the strength of the shear wave front 500 at the selected region of interest 510. Shear wave sources S1 and S2 are relatively far from the ROI, so they will be transmitted earlier; S5 is the nearest source and is therefore transmitted last. The shear waves from all sources will therefore reach the ROI at the same time to form a stronger wave front. The circular wave front 500 is centered on a focal point P. In one embodiment, the user may select the location of the focal point P. In other embodiments, the ultrasound imaging system automatically selects the location of the focal point P based on an indication of the region of interest 510.

In the example embodiment shown in FIG. 5, the shear wave sources S1, S2, S3, S4, S5 are located along a line 512 that is substantially parallel to the propagation direction of the push pulses transmitted by the transducer 216. The line 512 may be substantially perpendicular to the transducer 216. (As is illustrated below, the invention does not require the source line 512 to be straight but rather its geometry may depend on the desired shape of the sheer wave front to be generated.) The sequence of push pulses alternates the shear wave source between deep and shallow focus locations within the tissue while progressively moving the shear wave source toward a central focus location (at S5). In other words, the push pulses generate the shear wave sources in turn starting at the shallowest location (at S1), then at the deepest location (at S2), then at a next shallowest location (at S3), then at a next deepest location (at S4), then at the central focus location (at S5). An artisan will understand from the disclosure herein that other sequences are possible, including starting at the deepest focus location.

In one embodiment, delays between the transmission of push pulses are based on the respective times of flight between focus locations of the shear wave sources S1, S2, S3, S4, S5 and the focal point P. For example, the transducer 216 may transmit a first push pulse focused at S1 followed by a first delay. The first delay is equal to a difference between a first time of flight of a first shear wave 514 from S1 to the focal point P and a second time of flight of a second shear wave 516 from S2 to the focal point P. After the first delay, the transducer 216 transmits a second push pulse focused at S2, which is followed by a second delay.

Similarly, the second delay is equal to a difference between the second time of flight of the second shear wave 516 from S2 to the focal point P and a third time of flight of a third shear wave 518 from S3 to the focal point P. After the second delay, the transducer 216 transmits the third push pulse focused at S3, which is followed by a third delay. The third delay is equal to a difference between the third time of flight of the third shear wave 518 from S3 to the focal point P and a fourth time of flight of a fourth shear wave 520 from S4 to the focal point P. After the third delay, the transducer 216 transmits the fourth push pulse focused at S4, which is followed by a fourth delay. The fourth delay is equal to a difference between the fourth time of flight of the fourth shear wave 520 from S4 to the focal point P and a fifth time of flight of a fifth shear wave 522 from S5 to the focal point P. After the fourth delay, the transducer 216 transmits the fifth push pulse focused at S5.

The respective shear waves 514, 516, 518, 520, 522 interact with one another to form the circular wave front 500, which is centered at the focal point P. The focal point P may be inside or outside the ROI. Usually, P will be chosen to lie behind the ROI so that the high-intensity share wave front can cover the whole ROI. An artisan will recognize from the disclosure herein that other shapes may also be formed. For example, one or more focal points may be used to form wave fronts based on an ellipse, a parabola, or a hyperbola. In other embodiments, any other geometric shape or non-geometric shape may be formed.

Figure 6:
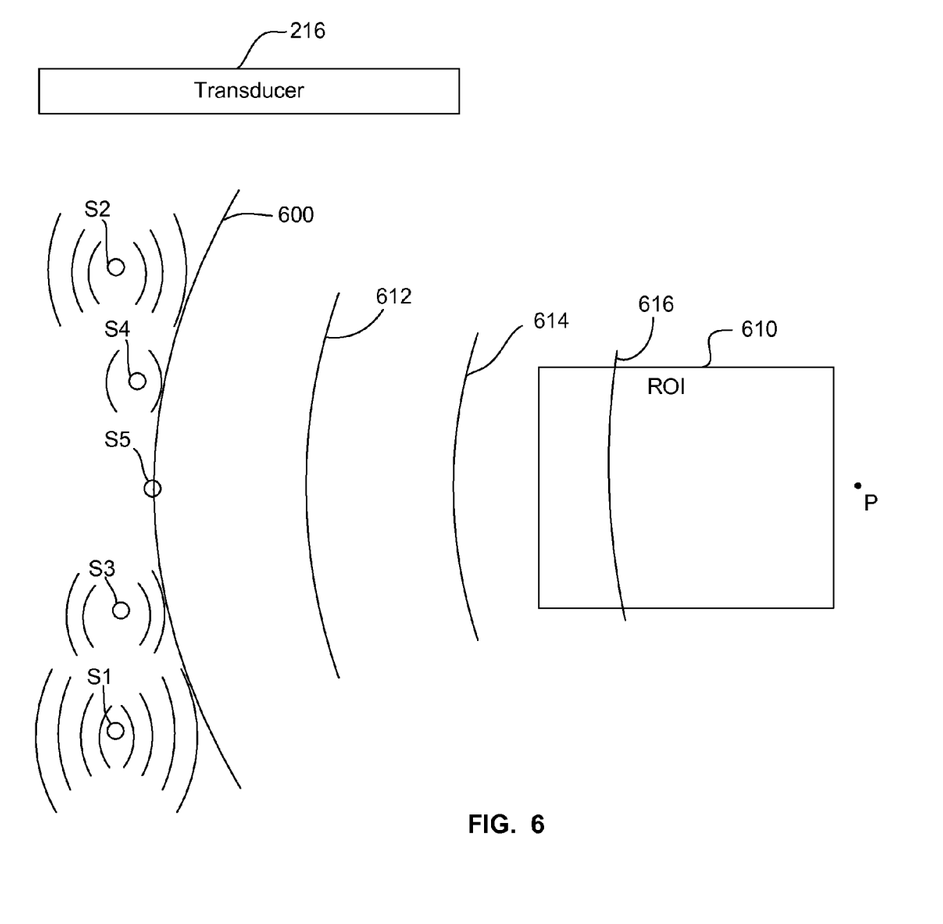
FIG. 6 is a schematic diagram illustrating shear wave sources generated within biological tissue according to another embodiment.

An artisan will also recognize from the disclosure herein that the focus locations do not necessarily need to be located along a straight line. For example, FIG. 6 is a schematic diagram illustrating shear wave sources S1, S2, S3, S4, S5 generated within biological tissue according to another embodiment. In this example embodiment, the focus locations are based on a rate of transmission or selected delays between the transmissions of the push pulses.

For example, the push pulses may be transmitted at a constant rate, say every 0.5 ms. If the shear wave propagating speed is about 2 m/s (2 mm/ms), then the shear wave travels about 1 mm every 0.5 ms. In the example shown in FIG. 6, a series of arcs 600, 612, 614, 616 that represent the desired shear wave front shape are shown co-centered at the focal point P, which is located outside of a selected region of interest 610. As with the example shown in FIG. 5, the sequence of push pulses alternates the shear wave source between deep and shallow focus locations within the tissue while progressively moving the shear wave source toward a central focus location (at S5). To form the desired shear wave front shape that propagates through the region of interest 610, the shear wave front source S5 is located on the arc 600 at a distance from the transducer 216 corresponding to the depth of the focal point P within the tissue. Then, the shear wave source S4 is located 1 mm from the arc 600, the shear wave source S3 is located 2 mm away from the arc 600, the shear wave source S2 is located 3 mm away from the arc 600, and the shear wave source S1 is located 4 mm away from the arc 600. For the selected sequence, the transducer 216 transmits a first push pulse focused at S1 at time zero, a second push pulse focused at S2 at time 0.5 ms, a third push pulse focused at S3 at time 1.0 ms, a fourth push pulse focused at S4 at time 1.5 ms, and a fifth push pulse focused at S5 at time 2.0 ms.

Figure 7:
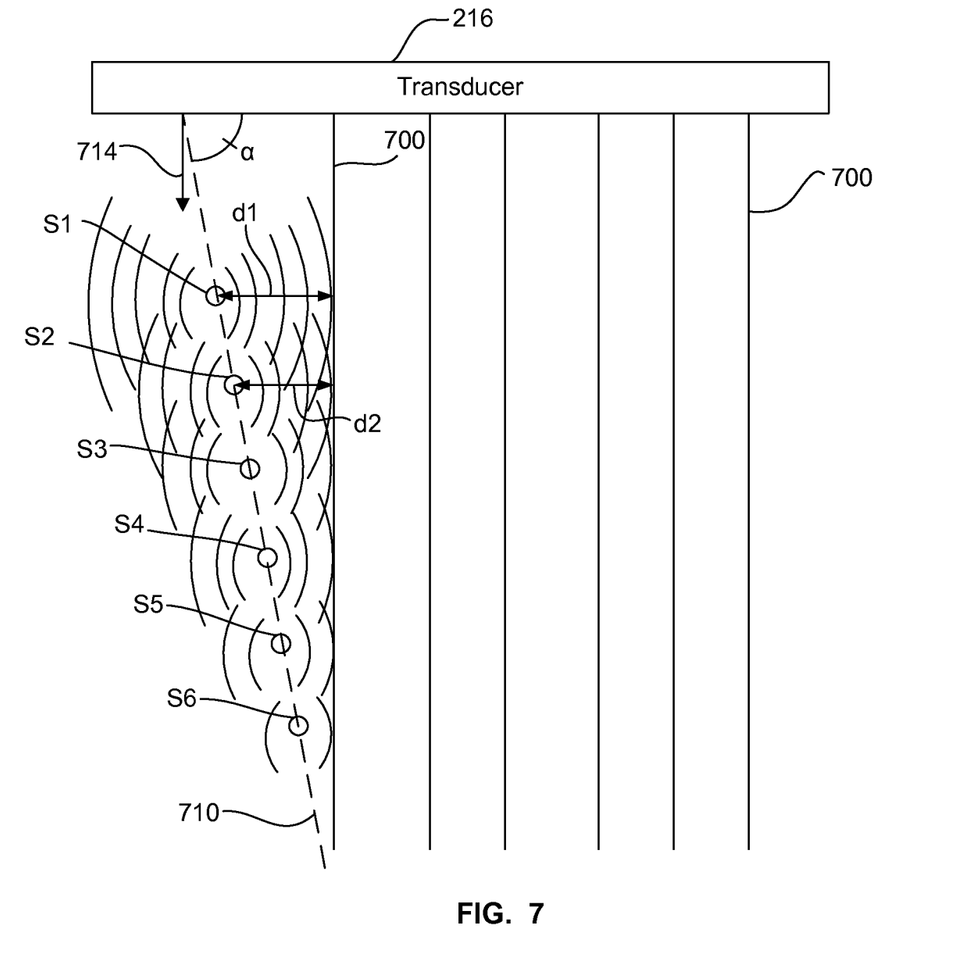
FIG. 7 is a schematic diagram illustrating shear wave sources generated within biological tissue to generate a planar shear wave front according to another embodiment.

FIG. 7 is a schematic diagram illustrating shear wave sources S1, S2, S3, S4, S5 generated within biological tissue to generate a planar shear wave front 700 according to another embodiment. In this example embodiment, the shear wave sources S1, S2, S3, S4, S5 are located along a straight line 710 that is offset at an angle $\alpha$ with respect to a propagation direction (indicated by arrow 714) of push pulses generated by the transducer 216. The angle $\alpha$ is selected in this example, based on the shear wave propagation speed, to generate the planar shear wave fronts 700 that are substantially perpendicular to the transmitting surface of the transducer 216. The sequence begins at the shallowest location (at S1) and progresses deeper into the tissue until it reaches the deepest location (at S6). In other words, the transducer 216 transmits a first push pulse focused at S1, a second push pulse focused at S2, a third push pulse focused at S3, a fourth push pulse focused at S4, and a fifth push pulse focused at S5. The transmit times of the push pulses are calculated from the relative positions of the shear wave sources S1, S2, S3, S4, S5 along the line 710, the respective depths of the focus locations, and the shear wave propagation speed. An artisan will recognize from the disclosure herein that the sequence may be reversed by transmitting push pulses from deepest to shallowest focus locations and tilting the line 710 in the opposite direction. Further, the shear wave fronts 700 may be tilted by changing the rate at which the transducer 216 transmits the push pulses and/or the angle $\alpha$.

Consider FIG. 7 and an example of how the system can compute the needed positions and generation times of the various sources S1, S2, S3, . . . . In FIG. 7, the desired wavefront 700 is a "vertical line" viewed as in the figure, that is, lines of constant azimuth, in this case, perpendicular to the transducer 216 face. Let d1, d2 be the distances from the chosen source line 710 at source points S1, S2, respectively, to the left-most line 700 (again, as shown in FIG. 7) and let $v_s$ be the shear wave propagation speed for the tissue. It will therefore take the shear wave from source S1 approximately a time $t1=d1/v_s$ to travel from the chosen source line 512 to the left-most line 700, and it will take the shear wave from source S2 approximately a time $t2=d2/v_s$ to do the same. For the two shear waves from S1 and S2 to arrive at the left-most line 700 at the same time, S2 will therefore need to be generated (t1-t2) after S1. Similar computations can be done for the remaining source points S3-S6. Note that this procedure does not require the source line 710 to be straight (FIG. 6 illustrates this), although in many cases this will be the easiest choice to implement since it doesn't require a change of TX azimuth.

This disclosure is thus not limited to the example shear wave front shapes, push pulse focus locations, delays, transmission rates, or other parameters discussed herein. Indeed, any shear wave front shape may be generated by appropriate selection of shear wave source locations, the sequence of transmitting push pulses to the selected locations, and the timing between push pulses. Such selections may be based on the location and dimensions of the region of interest, the propagation speed of the push pulses through the tissue, the propagation speed of the shear waves through the tissue, and/or the desired strength of the shear wave front as it passes through the region of interest.

It will be understood by those having skill in the art that many changes may be made to the details of the above-described embodiments without departing from the underlying principles of the invention. The scope of the present invention should, therefore, be determined only by the following claims.

The invention claimed is:

1. A method for imaging viscoelasticity in biological tissue using a dynamically controlled shear wave front produced by an ultrasound imaging system, the method comprising:
    receiving an indication of a region of interest within the tissue;
    selecting a shape of the shear wave front to pass through the region of interest;
    selecting, based on the selected shear wave front shape, a plurality of focus locations within the tissue and a sequence in which to move a shear wave source between the selected focus locations, wherein the sequence includes alternating the shear wave source locations, with respect to one another, between deep and shallow focus locations within the tissue while progressively moving the shear wave source toward a central focus location;
    transmitting, into the tissue, a series of focused ultrasonic push pulses from a transducer array based on the selected sequence, wherein each push pulse remotely generates a respective shear wave at one of the selected focus locations, and wherein the respectively generated shear waves interact with one another as the shear wave source moves between the focus locations to produce an overall shear wave having the selected shear wave front shape; and
    imaging, using the transducer array, the shear wave front as it travels through the region of interest.

2. The method of claim 1, wherein selecting the shear wave front shape comprises selecting a shape configured to increase a shear wave strength at the region of interest.

3. The method of claim 1, further comprising selecting a focal point within the tissue, wherein the selected shear wave front shape corresponds to a substantially circular arc centered at the focal point.

4. The method of claim 3, wherein selecting the plurality of focus locations comprises defining the plurality of focus locations along a straight line substantially parallel to a propagation direction of the push pulses.

5. The method of claim 4, wherein transmitting the push pulses comprises:
    transmitting a first push pulse focused at a first focus location;
    delaying transmission of a second push pulse after said transmitting of the first push pulse, the second push pulse focused at a second focus location, wherein the delay is for a time period substantially equal to a difference between a first time of flight and a second time of flight, the first time of flight corresponding to a first shear wave traveling between the first focus location and the focal point, and the second time of flight corresponding to a second shear wave traveling between the second focus location and the focal point; and
    after the delay, transmitting the second push pulse.

6. The method of claim 3, wherein selecting the plurality of focus locations comprises defining the plurality of focus locations along a curved path within the tissue.

7. The method of claim 6, where the curved path is based on transmitting the series of push pulses at a constant rate so as to generate the substantially circular arc of the overall shear wave.

8. The method of claim 7, wherein selecting the plurality of focus locations further comprises:
defining an arc of the circular shear wave front shape;
placing a first focus location on the arc at a first depth within the tissue corresponding to a depth of the focal point; and
placing a second focus location at a second depth within the tissue and at a distance from the arc corresponding to a propagation delay based on the constant rate used to transmit the series of push pulses.

9. The method of claim 1, wherein selecting the plurality of focus locations comprises defining the plurality of focus locations along a straight line offset at an angle with respect to a propagation direction of the push pulses.

10. The method of claim 9, wherein transmitting the push pulses comprises:
transmitting the series of push pulses at respective times such that the shear wave front shape is planar.

11. The method of claim 1, wherein receiving an indication of a region of interest comprises:
generating, using the ultrasound imaging system, a B-mode ultrasound image of the tissue; and
allowing a user to place a marker on the B-mode ultrasound image to define the region of interest.

12. The method of claim 1, further comprising weighting one or more of the transmitted push pulses.

13. An ultrasound system for imaging viscoelasticity in biological tissue using a dynamically controlled shear wave front produced by an ultrasound imaging system, the system comprising:
a processor;
an ultrasound transducer comprising an array of electroacoustic elements; and
a shear wave subsystem configured to:
receive an indication of a region of interest within the tissue;
select a shape of the shear wave front to pass through the region of interest;
select, based on the selected shear wave front shape, a plurality of focus locations within the tissue and a sequence in which to move a shear wave source between the selected focus locations, wherein the sequence includes alternating the shear wave source locations, with respect to one another, between deep and shallow focus locations within the tissue while progressively moving the shear wave source toward a central focus location;
transmit, into the tissue, a series of focused ultrasonic push pulses from the transducer based on the selected sequence, wherein each push pulse remotely generates a respective shear wave at one of the selected focus locations, and wherein the respectively generated shear waves interact with one another as the shear wave source moves between the focus locations to produce an overall shear wave having the selected shear wave front shape; and
image, using the transducer, the shear wave front as it travels through the region of interest.

14. The system of claim 13, wherein the shear wave subsystem selects the shear wave front shape by selecting a shape configured to increase a shear wave strength at the region of interest.

15. The system of claim 13, wherein the shear wave subsystem is further configured to select a focal point within the tissue, wherein the selected shear wave front shape corresponds to a substantially circular arc centered at the focal point.

16. The system of claim 15, wherein the shear wave subsystem selects the plurality of focus locations by defining the plurality of focus locations along a straight line substantially parallel to a propagation direction of the push pulses.

17. The system of claim 16, wherein the shear wave subsystem transmits the push pulses using the transducer by:
transmitting a first push pulse focused at a first focus location;
delaying transmission of a second push pulse after said transmitting of the first push pulse, the second push pulse focused at a second focus location, wherein the delay is for a time period substantially equal to a difference between a first time of flight and a second time of flight, the first time of flight corresponding to a first shear wave traveling between the first focus location and the focal point, and the second time of flight corresponding to a second shear wave traveling between the second focus location and the focal point; and
after the delay, transmitting the second push pulse.

18. The system of claim 15, wherein the shear wave subsystem selects the plurality of focus locations by defining the plurality of focus locations along a curved path within the tissue.

19. The system of claim 18, where the curved path is based on transmitting the series of push pulses at a constant rate so as to generate the substantially circular arc of the overall shear wave.

20. The system of claim 19, wherein the shear wave subsystem further selects the plurality of focus locations by:
defining an arc of the circular shear wave front shape;
placing a first focus location on the arc at a first depth within the tissue corresponding to a depth of the focal point; and
placing a second focus location at a second depth within the tissue and at a distance from the arc corresponding to a propagation delay based on the constant rate used to transmit the series of push pulses.

21. The system of claim 13, wherein the shear wave subsystem selects the plurality of focus locations by defining the plurality of focus locations along a straight line offset at an angle with respect to a propagation direction of the push pulses.

22. The system of claim 21, wherein the shear wave subsystem transmits the push pulses by transmitting the series of push pulses at respective times such that the shear wave front shape is planar.

23. The system of claim 13, wherein the shear wave subsystem receives an indication of a region of interest by:
generating, using the ultrasound imaging system, a B-mode ultrasound image of the tissue; and
allowing a user to place a marker on the B-mode ultrasound image to define the region of interest.

24. The system of claim 13, where the shear wave subsystem is further configured to weight one or more of the transmitted push pulses.

25. A non-transitory computer-readable medium having stored thereon computer-executable instructions for performing a method for imaging viscoelasticity in biological tissue using a dynamically controlled shear wave front produced by an ultrasound imaging system, the method comprising:
- receiving an indication of a region of interest within the tissue;
- selecting a shape of the shear wave front to pass through the region of interest;
- selecting, based on the selected shear wave front shape, a plurality of focus locations within the tissue and a sequence in which to move a shear wave source between the selected focus locations, wherein the sequence includes alternating the shear wave source locations, with respect to one another, between deep and shallow focus locations within the tissue while progressively moving the shear wave source toward a central focus location;
- transmitting, into the tissue, a series of focused ultrasonic push pulses from a transducer array based on the selected sequence, wherein each push pulse remotely generates a respective shear wave at one of the selected focus locations, and wherein the respectively generated shear waves interact with one another as the shear wave source moves between the focus locations to produce an overall shear wave having the selected shear wave front shape; and
- imaging, using the transducer array, the shear wave front as it travels through the region of interest.

26. A system for imaging viscoelasticity in biological tissue using a dynamically controlled shear wave front produced by an ultrasound imaging system, the system comprising:
- means for receiving an indication of a region of interest within the tissue;
- means for selecting a shape of the shear wave front to pass through the region of interest;
- means for selecting, based on the selected shear wave front shape, a plurality of focus locations within the tissue and a sequence in which to move a shear wave source between the selected focus locations, wherein the sequence includes alternating the shear wave source locations, with respect to one another, between deep and shallow focus locations within the tissue while progressively moving the shear wave source toward a central focus location;
- means for transmitting, into the tissue, a series of focused ultrasonic push pulses based on the selected sequence, wherein each push pulse remotely generates a respective shear wave at one of the selected focus locations, and wherein the respectively generated shear waves interact with one another as the shear wave source moves between the focus locations to produce an overall shear wave having the selected shear wave front shape; and
- means for imaging the shear wave front as it travels through the region of interest.

* * * * *